(12) United States Patent
Carr (10) Patent No.: US 11,344,648 B2
(45) Date of Patent: May 31, 2022

(54) SYSTEM AND METHOD FOR AIR PURIFICATION AND STERILIZATION

(71) Applicant: Nathan Carr, Phenix City, AL (US)

(72) Inventor: Nathan Carr, Phenix City, AL (US)

(73) Assignee: Ventorlux, LLC, Phenix City, AL (US)

( * ) Notice: Subject to any disclaimer, the term of this patent is extended or adjusted under 35 U.S.C. 154(b) by 44 days.

(21) Appl. No.: 16/788,211

(22) Filed: Feb. 11, 2020

(65) Prior Publication Data

US 2020/0254133 A1    Aug. 13, 2020

Related U.S. Application Data

(60) Provisional application No. 62/803,783, filed on Feb. 11, 2019.

(51) Int. Cl.
*A61L 9/20* (2006.01)

(52) U.S. Cl.
CPC ............. *A61L 9/20* (2013.01); *A61L 2209/11* (2013.01); *A61L 2209/12* (2013.01); *A61L 2209/15* (2013.01); *A61L 2209/16* (2013.01)

(58) Field of Classification Search
None
See application file for complete search history.

(56) References Cited

U.S. PATENT DOCUMENTS

| 2006/0201119 A1* | 9/2006 | Song ................. B01D 46/0024 55/471 |
|---|---|---|
| 2008/0031735 A1 | 2/2008 | Chen |
| 2009/0129974 A1 | 5/2009 | McEllen |
| 2012/0183443 A1 | 7/2012 | Hurley |
| 2017/0246576 A1* | 8/2017 | Jung ................. B01D 46/0005 |
| 2018/0356109 A1* | 12/2018 | Nomura .................... A61L 9/20 |

FOREIGN PATENT DOCUMENTS

| CN | 201448265 U | 5/2010 |
|---|---|---|
| CN | 203395894 U | 1/2014 |

* cited by examiner

*Primary Examiner* — Jelitzam Perez
(74) *Attorney, Agent, or Firm* — Jeremy A. Smith, Esq.; Lanier Ford Shaver & Payne, PC (57) ABSTRACT

A system and method for an air purification assembly that creates high volume, sterilized straight-line airflow with a significant reduction in electricity consumption utilizing counter rotation of two propellers mounted in reverse to create linear airflow and thrust that sucks in air through an inlet and blows the air out through an outlet. Air purification assembly may also sterilize the air as it passes through light utilizing a light core system with a ring-shaped assembly that has one or more UV-C LEDs that may kill bio-organisms within proximity to the air purification assembly while dissipating the heat created by the UVC LED lights in the light core system.

16 Claims, 9 Drawing Sheets

FIG. 9

SYSTEM AND METHOD FOR AIR PURIFICATION AND STERILIZATION

CROSS REFERENCE TO RELATED APPLICATIONS

This application is a non-provisional application which claims priority to U.S. Provisional Application No. 62/803,783 filed on Feb. 11, 2019, which is incorporated by reference in its entirety.

FIELD OF THE DISCLOSURE

This disclosure relates generally to the field of air blower assemblies, and more specifically to a dual rotor system and apparatus for high output and the removal of contaminants from air.

BACKGROUND

Indoor air quality has increasingly become an important issue as public health knowledge has increased as well as demand for sterile environments. Particularly, many pathogens such as viruses, molds and bacteria are now known health risk. Further, in traditional fan assemblies these pathogens are known to multiply and be circulated.

There have been several attempts to solve the problems in the prior art to purify air in environments where clean air is desired. Some examples include air purifying devices that use ultraviolet light, such as UV-V or UV-C, to decontaminate air passing through a fan assembly. These devices often connect to home heating and air-condition systems to sterilize air being circulated in a home. Other examples have their own blower capabilities and often use an UV-V light emitting source, into a destratification fan, to catalyze an oxidation reaction inserted into a destratification fan.

However, traditional air purifying devices are often stationary and are capable of purifying the air on a predetermined area. The devices that are portable, or that can quickly be moved and installed, often are not capable of quickly purifying large volumes of air. Further these devices often sterilize air by catalyzing an oxidation reaction and not use a specific wavelength to the kill the pathogens.

Due to all of the existing shortcoming in presently available devices, there is still a need for an air purifying device having a large volume capability that is also easily transportable.

SUMMARY

The preceding and following embodiments and descriptions are for illustrative purposes only and are not intended to limit the scope of this disclosure. Other aspects and advantages of this disclosure will become apparent from the following detailed description.

The present invention is directed to an air purification assembly comprising, an inlet and an outlet, a housing component having a first end and a second end, a funnel having a first end and second end, the outlet at the first end of the funnel, the second end of the funnel connected to the second end of to the housing component, a first hub assembly having a first motor and a first rotor, the first rotor having one or more blades, a second hub assembly having a second motor and a second rotor, the second rotor having one or more blades, one or more guide slots positioned along an inner circumference of the housing component wherein the first hub assembly and the second hub assembly are slidably engaged with the one or more guide slots, one or more conductive spacers positioned in the one or more guide slots, wherein the one or more conductive spacers are configured to transfer electricity between the first motor and the second motor, further comprising an end cap, the end cap connected to the housing component at the first end, the end cap having one or more grooves configured to allow air to be sucked into the air purification assembly by the second motor, wherein the blades of the second rotor are orientated at a greater angle than the blades of the first rotor, wherein the second blades are at a 45-degree angle and the first blades are at a 29 degree angle, wherein the blades of the first rotor and the second rotor are configured to rotate counterclockwise, wherein the first motor and the second motor are electric motors, further comprising an end cone cap, the end cone cap connected to the first motor, the end cone cap facing towards the outlet wherein cone cap is configured to provide further pressuring of the air after it is blown by the first rotor by compressing the air between the end cone cap and the funnel as it is blown out the outlet, further comprising a ring-shaped assembly configured to attach around an outer circumference of said second motor, wherein the ring-shaped assembly has one or more UV-C LED.

The present invention is also directed to an air purification assembly comprising a ring-shaped assembly, wherein the ring-shaped assembly further has one or more UV-C LED, further comprising a driver wherein the UV-C LED communicate with the driver via a bus, the driver further configured to adjust the output of the UV-C LED, the driver further configured to turn off or on the UV-C LED in specific increments of time, further comprising one or more flat spaces running the length of the ring-shaped assembly, each flat space holding one or more heat sinks having a PCB board and an individual UV-C LED, further comprising aluminum tape configured to reflect light from the UVC LEDs back towards a center of the air purification assembly, further comprising an inlet and an outlet, a housing component having a first end and a second end, a funnel having a first and second end, the outlet at the first end of the funnel, the second end of the funnel connected to the second end of the housing component, a first hub assembly having a first motor and a first rotor, the first rotor having one or more blades, a second hub assembly having a second motor and a second rotor, the second rotor having one or more blades, and one or more guide slots positioned along an inner circumference of the housing component wherein the first hub assembly and the second hub assembly are slidably engaged with the one or more guide slots, further comprising one or more conductive spacers positioned in the one or more guide slots, wherein the one or more conductive spacers are configured to transfer electricity between the first motor and the second motor, further comprising: an end cap, the end cap connected to housing component at the first end, the end cap having one or more grooves configured to allow air to be sucked in by the second motor, wherein the second blades are at a 45-degree angle and the first blades are at a 29 degree angle, the first blades and the second blades rotating counterclockwise, the first and the second blades facing opposite of each other.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises", and grammatical equivalents thereof are used herein to mean that other components, ingredients, steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and upper limit is the second number. For example, 25 to 100 mm means a range whose lower limit is 25 mm and upper limit is 100 mm.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The present description is directed to a system and method for a highly efficient and environmentally sound air purification assembly that creates high volume, sterilized straight-line airflow that may be used in buildings and other spaces with a significant reduction in electricity consumption. Air purification assembly utilizes counter rotation of two propellers mounted in reverse to create linear airflow and thrust that sucks in air through an inlet and blows the air out through an outlet.

Air purification assembly may also sterilize the air as it passes through light utilizing a light core system. The light core system may have a ring-shaped assembly that has one or more UV-C LEDs. The air purification assembly may include a housing having two hub assemblies, wherein each hub assembly has an electric motor and a rotor, one of the motors is designed to accept the ring-shaped assembly. With the light core system built into or otherwise connected to air purification assembly the system may kill bio-organisms within proximity to the air purification assembly while dissipating the heat created by the UVC LED lights in light core system 115.

Figure 1:
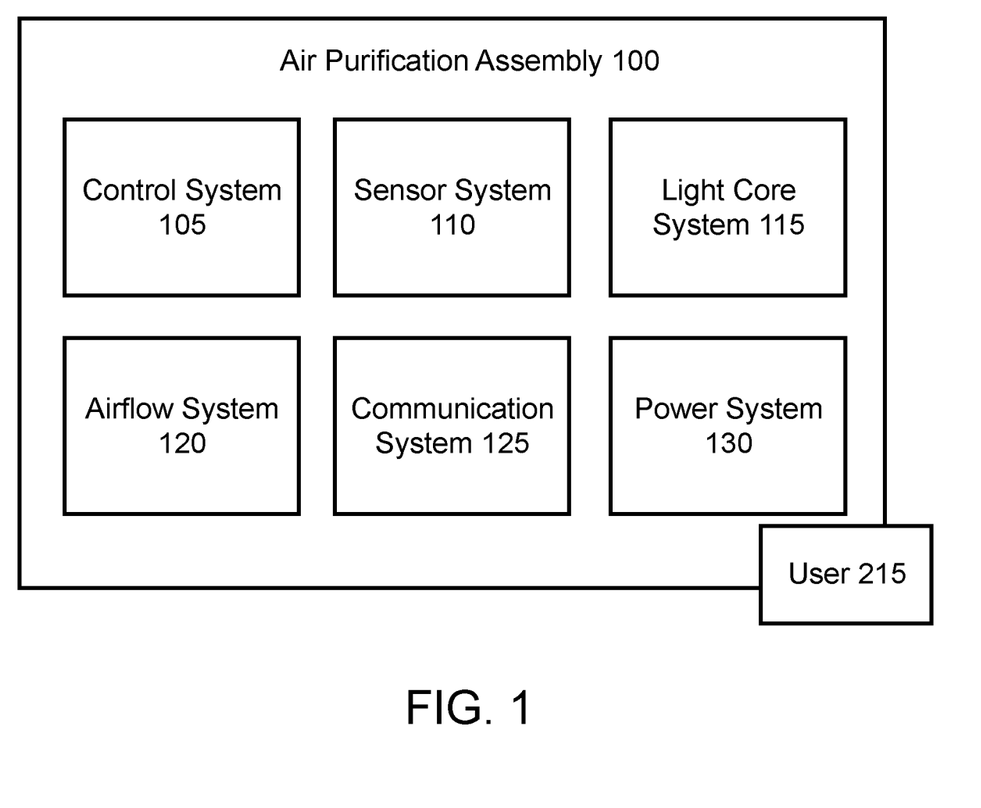
FIG. 1 shows a block diagram of the various systems of the air purification assembly according to various aspects of the present disclosure.

With reference now to FIG. 1, FIG. 1 illustrates a block diagram of one exemplary embodiment of subsystems of air purification assembly 100. Air purification assembly 100 may have a plurality of systems including a control system 105, a sensor system 110, a light core system 115, an airflow system 120, a communication system 125, and a power system 130, which may be integrated in combination within the structure of air purification assembly 100. The various systems may be individually configured and correlated with respect to each other so as to attain the desired objective.

Power system 130 of air purification assembly 100 provides the energy to light core system 115, airflow system 120, sensor system 110, and the circuits and components of control system 105 during the process of airflow and sterilization. Air purification assembly 100 may be powered by methods known by those of ordinary skill in the art. In some embodiments, Air purification assembly 100 may plug into an electrical outlet using an electrical cord to supply power to light core system 115, airflow system 120, sensor system 110, and the circuits and components of control system 105. Further power system 130 may include a rechargeable battery pack whereby the rechargeable battery is of a charge, design, and capacity, to provide sufficient power light core system 115, airflow system 120, sensor system 110, and the circuits and components of control system 105 while running air purification assembly 100 for a set period to provide sterilized airflow to an environment.

Control system 105 may operate to control the actuation of the other systems. Control system 105 may have a series of computing devices which will be discussed in detail later in the description. Control system 105 may be in the form of, a circuit board, a memory or other non-transient storage medium in which computer-readable coded instructions are stored and one or more processors configured to execute the instructions stored in the memory. Control system 105 may have a wireless transmitter, a wireless receiver, and a related computer process executing on the processors.

Computing devices of control system 105, may be any type of computing device that typically operate under the control of one or more operating systems, which control scheduling of tasks and access to system resources. Computing devices may be a phone, tablet, television, desktop computer, laptop computer, networked router, networked switch, networked, bridge, or any computing device capable of executing instructions with sufficient processor power and memory capacity to perform operations of control system 105.

The one or more computing devices may be integrated into control system 105, while in other non-limiting embodiments, control system 105 may be a remotely located computing device or server configured to communicate with one or more other control systems 105. Control system 105 may also include an internet connection, network connection, and/or other wired or wireless means of communication (e.g., LAN, etc.) to interact with other components. The connection allows a user to update, control, send/retrieve information, monitor or otherwise interact passively or actively with control system 105.

Control system 105 may include control circuitry and one or more microprocessors, drivers, or controllers acting as a servo control mechanism capable of receiving input from sensor system 110 and communication system 125, analyzing the input from sensor system 110 and communication system 125, and generating an output signal to light core system 115, airflow system 120, and power system 130. The microprocessors may have on-board memory to control the power that is applied to light core system 115, airflow system 120, communication system 125, and power system 130, in response to input signals from user and from sensor system 110.

Control system 105 may include circuitry to provide an actuable interface for a user to interact with, including switches and indicators and accompanying circuitry for an electronic control panel or mechanical control panel. Such an actuable interface may present options to a user to select from such as, without limitation, controlling the motors and UV-C LED. Control system 105 may be preprogrammed with any references values, by any combination hardwiring, software, firmware to implement various operational modes including but not limited to temperature, light, and humidity values.

The microprocessors in control system 105 may also monitor the current state of circuitry within control system 105 to determine the specific mode of operation chosen by the user. For instance, when "on", the microprocessors may begin autonomously provide sterilized airflow. Further, such microprocessors that may be part of control system 105 may receive signals to light core system 115, airflow system 120, communication system 125, and power system 130, to provide self-diagnosis such as if whether any of the components in the various systems need to be replaced, whether the UV-C LEDs have been depleted, as well as when the targeted location has been sanitized.

Figure 2:
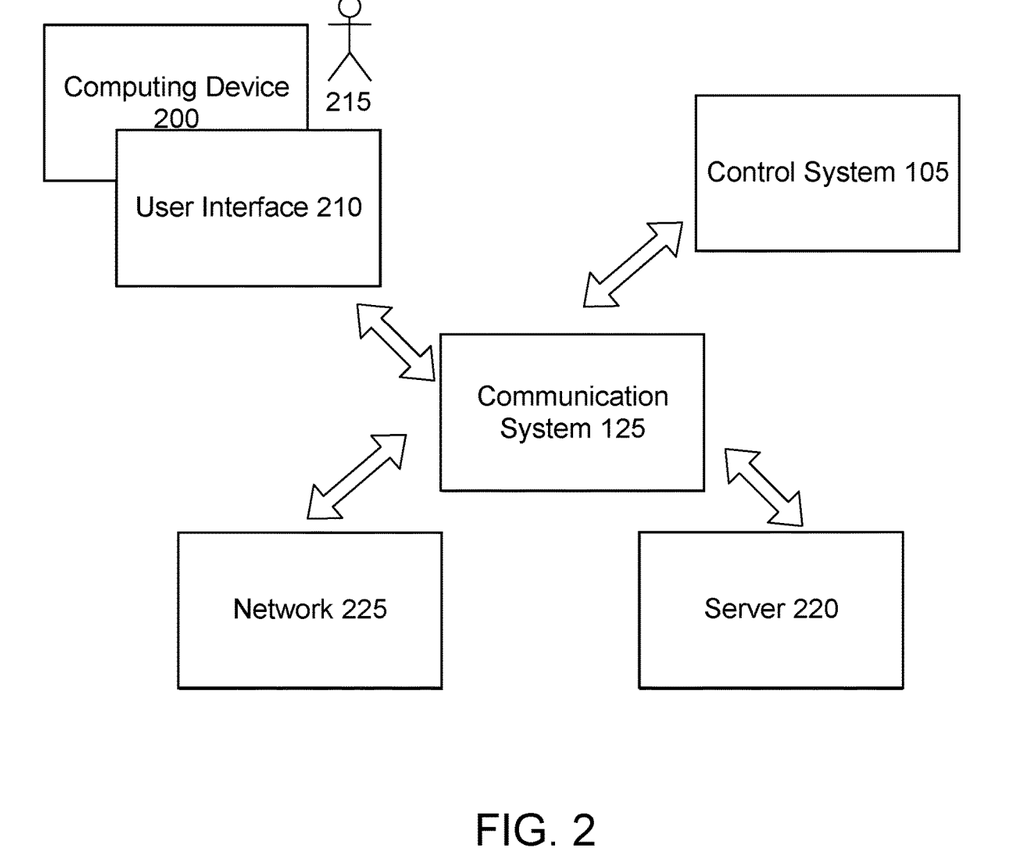
FIG. 2 shows an exemplary block diagram of communication system of the air purification assembly.

Control system 105 may be in communication with communication system 125, as illustrated in FIG. 2 to connect with other or computing devices whereby signals transmitted from the computing devices may be received by control system 105. Communication system 125 may allow a user such as user 215 to interact with control system 105 using a computing device such as computing device 200 even if user 215 is not proximate to control system 105. User 215 may access user interface 210 using computing device 200. User interface 210 may have a plurality of buttons or icons that are selectable by user for communication system 125 to perform particular processes in response to the selections. In one or more non-limiting embodiments, communication system 125 may be innate, built into, or otherwise integrated into existing platforms or systems such as a website, a third party program, Apple™ operating systems (e.g. iOS), Android™ Snapchat™, Instagram™, Facebook™, or any other platform.

Computing device 200 of communication system 125 may be similar to the computing devices of control system 105 and may be any type of computing device that typically operates under the control of one or more operating systems, which control scheduling of tasks and access to system resources. Computing device 200, may in some embodiments, be a computing device such as an iPhone™, Android-based phone, or Windows-based phone, a tablet, television, desktop computer, laptop computer, gaming system, wearable device electronic glasses, networked router, networked switch, networked, bridge, or any computing device capable of executing instructions with sufficient processor power and memory capacity to perform operations of Password code generation system 100 while in communication with network. Computing device 200 may have location tracking capabilities such as Mobile Location Determination System (MLDS) or Global Positioning System (GPS) whereby they may include one or more satellite radios capable of determining the geographical location of computing device 200.

In some embodiments computing devices 200 may be in communication with one or more servers such as server 220 via communication system 125 or one or more networks such as network 225 connected to communication system 125. Server 220 may be located at a data center, or any other location suitable for providing service to network 225 whereby server 220 may be in one central location or in many different locations in multiple arrangements. Server 220 may comprise a database server such as MySQL® or Maria DB® server. Server 220 may have an attached data storage system storing software applications and data. Server 220 have may a number of modules that provide various functions related to communication system 125. Modules may be in the form of software or computer programs that interact with the operating system of server 220 whereby data collected in databases as instruction-based expressions of components and/or processes under communication system 125 may be processed by one or more processors within server 220 or another component of communication system 125 as well as in conjunction with execution of one or more other computer programs.

Modules may be configured to receive commands or requests from computing devices 200, server 220, and outside connected devices over network 225. Server 220 may comprise components, subsystems and modules to support one or more management services for communication system 125.

In one or more non-limiting embodiments, network 225 may include a local area network (LAN), such as a company Intranet, a metropolitan area network (MAN), or a wide area network (WAN), such as the Internet or World Wide Web. Network 225 may be a private network or a public network, or a combination thereof. Network 225 may be any type of network known in the art, including telecommunications network, a wireless network (including Wi-Fi), and a wire-line network. Network 225 may include mobile telephone networks utilizing any protocol or protocols used to communicate among mobile digital computing devices (e.g.

computing device 200), such as GSM, GPRS, UMTS, AMPS, TDMA, or CDMA. In one or more non-limiting embodiments, different type of data may be transmitted via network 225 via different protocols. In alternative embodiments, computing devices 200, may act as standalone devices or whereby they may operate as peer machine in a peer-to-peer (or distributed) network environment.

Network 225 may further include a system of terminals, gateways, and routers. Network may employ one or more cellular access technologies including 2nd (2G), 3rd (3G), 4th (4G), 5th (5G), LTE, Global System for Mobil communication (GSM), General Packet Radio Services (GPRS), Enhanced Data GSM Environment (EDGE), and other access technologies that may provide for broader coverage between computing devices if for instance they are in a remote location not accessible by other networks.

Figure 3:
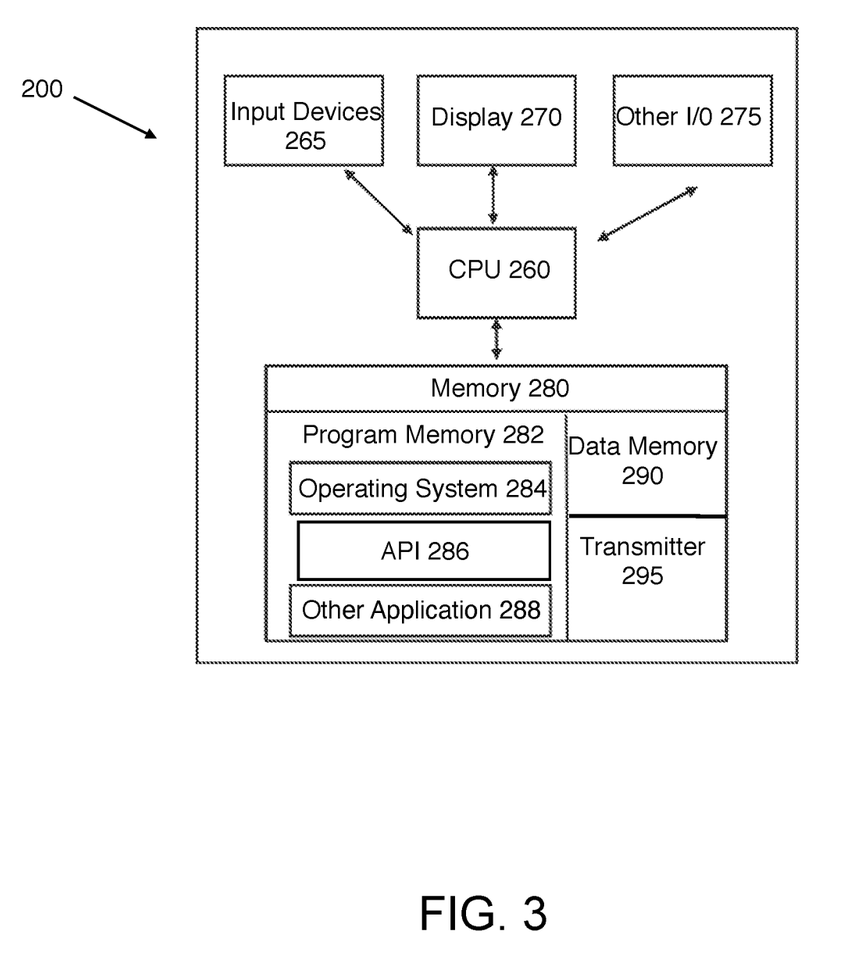
FIG. 3 shows a block diagram of a computing device according to various aspects of the present disclosure.

Turning to FIG. 3, FIG. 3 is a block diagram showing various components of computing device 200. Computing device 200 may comprise a housing for containing one or more hardware components that allow access to edit and query communication system 125. User Computing device 200 may include one or more input devices such as input devices 265 that provide input to a CPU (processor) such as CPU 260 of actions related to user 215. Input devices 265 may be implemented as a keyboard, a touchscreen, a mouse, via voice activation, wearable input device, a camera a trackball, a microphone, a fingerprint reader, an infrared port, a controller, a remote control, a fax machine, and combinations thereof.

The actions may be initiated by a hardware controller that interprets the signals received from input device 265 and communicates the information to CPU 260 using a communication protocol. CPU 260 may be a single processing unit or multiple processing units in a device or distributed across multiple devices. CPU 260 may be coupled to other hardware devices, such as one or more memory devices with the use of a bus, such as a PCI bus or SCSI bus. CPU 260 may communicate with a hardware controller for devices, such as for a display 270. Display 270 may be used to display text and graphics. In some examples, display 270 provides graphical and textual visual feedback to a user.

In one or more embodiments, display 270 may include an input device 265 as part of display 270, such as when input device 265 is a touchscreen or is equipped with an eye direction monitoring system. In some implementations, display 270 is separate from input device 265. Examples of display 270 include but are not limited to: an LCD display screen, an LED display screen, a projected, holographic, virtual reality display, or augmented reality display (such as a heads-up display device or a head-mounted device), wearable device electronic glasses, contact lenses capable of computer-generated sensory input and displaying data, and so on. Display 270 may also comprise a touch screen interface operable to detect and receive touch input such as a tap or a swiping gesture. Other I/O devices such as I/O devices 275 may also be coupled to the processor, such as a network card, video card, audio card, USB, FireWire or other external device, camera, printer, speakers, CD-ROM drive, DVD drive, disk drive, or Blu-Ray device. In further non-limiting embodiments, a display may be used as an output device, such as, but not limited to, a computer monitor, a speaker, a television, a smart phone, a fax machine, a printer, or combinations thereof.

CPU 260 may have access to a memory such as memory 280. Memory 280 may include one or more of various hardware devices for volatile and non-volatile storage and may include both read-only and writable memory. For example, memory 280 may comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. Memory 280 may be a non-transitory memory.

Memory 280 may include program memory such as program memory 282 capable of storing programs and software, including an operating system, such as operating system 284. Memory 280 may further include an application programming interface (API), such as API 286, and other computerized programs or application programs such as application programs 288. Memory 280 may also include data memory such as data memory 290 that may include database query results, configuration data, settings, user options, user preferences, or other types of data, which may be provided to program memory 282 or any element of user computing device 115.

Computing device 200 may have a transmitter 295, such as transmitter 295, to transmit the biological data. Transmitter 295 may have a wired or wireless connection and may comprise a multi-band cellular transmitter to connect to the server 220 over 2G/3G/4G cellular networks. Other embodiments may also utilize Near Field Communication (NFC), Bluetooth, or another method to communicate information.

Figure 4:
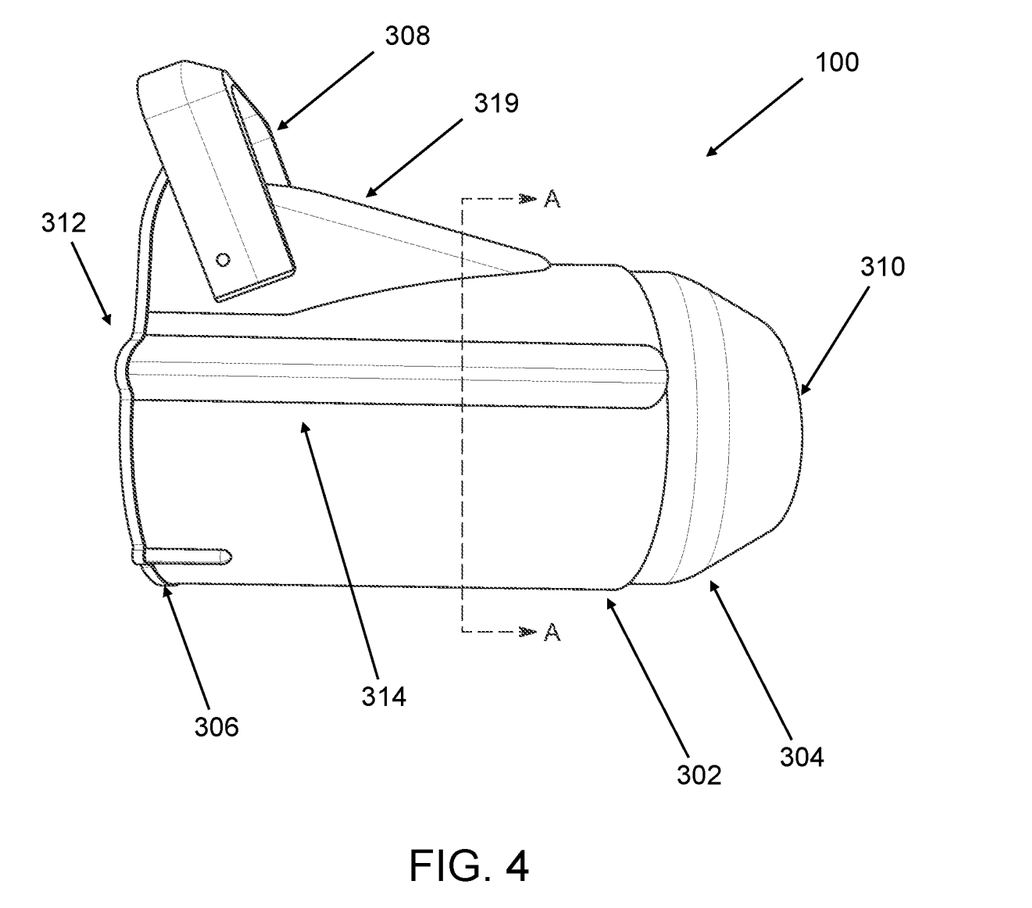
FIG. 4 shows an illustration of the air purification assembly.

With reference now to FIG. 4, FIG. 4 illustrates one embodiment of an air purification assembly 100 according to the present invention. Air purification assembly 100 may include a tubular shaped housing 302, an inlet end 312, an outlet end 310, an end cap 306, one or more guide slots 314, a top mount 319, and a funnel 304. Tubular shaped housing 302 may be hollow with a tubular shape. However this is non-limiting and housing may be other shapes such as a rectangle, square, hexagon, or octagon. Tubular shaped housing 302 may be made out of any plastic, metal, wood, natural or synthetic material. Guide slots 314 may be elongated and semi-tubular shape whereby guide slots 314 are positioned along the outside surface of tubular shaped housing 302.

Top mount 319 may be a hollow wedge-shaped piece that attaches to the tubular shaped housing 302. In some embodiments top mount 319 may integral to tubular shaped housing 302. Top mount 319 may house the electronics of the air purification assembly 100 including any number of wires, batteries, switches, or computer components used to power and operate the air purification assembly 100. Top mount 319 may be attached to handle 308 whereby handle 308 allows an operator to carry the air purification assembly 100. In some non-limiting embodiments, handle 308 may act as an activation switch of power system 130 such that air purification assembly 100 may be turned on or off by the movement of handle 308 from a first position to a second position (parallel to a surface of tubular housing 302 and perpendicular to a surface of tubular housing 302).

Tubular shaped housing 302 may be connected to funnel 304. In some embodiments funnel 304 may integral to tubular shaped housing 302. Funnel 304 may be hollow with an end terminating into tubular shaped housing 302 and an end terminating into outlet end 310 as to allow the passage air through the air purification assembly 100 from outlet end 310 towards tubular shaped housing 302. Funnel 304 may be conical frustum in shape with outlet end 310 smaller in diameter than the diameter of end terminating into tubular shaped housing 302.

Air may be sucked through end cap 362 positioned at the end of tubular shaped housing opposite of funnel 304. End cap 362 is illustrated as circular in shape however may be a structure like a square, rectangle and rhombus or hexagonal or octagonal. End cap 362 may have a number of grooves whereby grooves are configured to allow air to be sucked into tubular shaped body 302.

Figure 5:
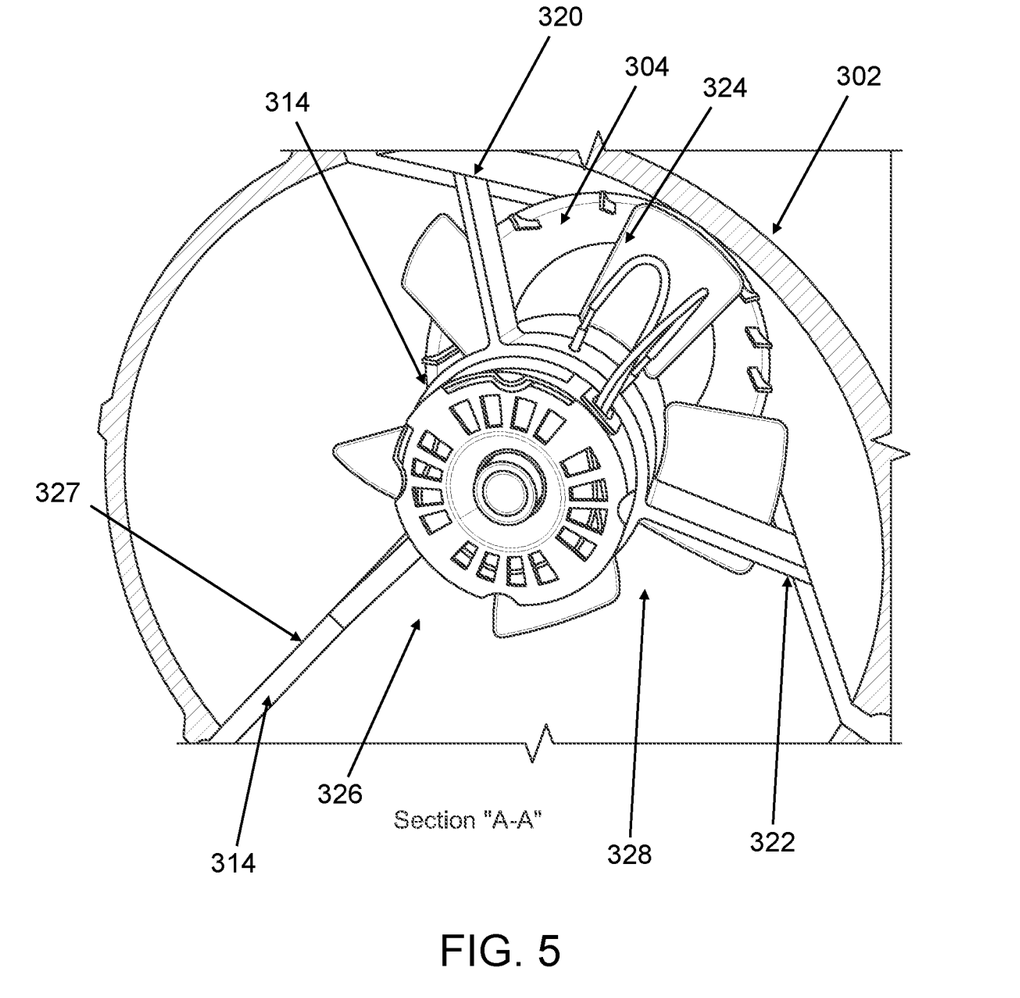
FIG. 5 shows a cross sectional view of the air purification assembly displaying the first hub assembly.

FIG. 5 is cross-sectional view of section A-A of FIG. 4. FIG. 5 illustrates tubular shaped housing 302, an interior view of the one or more guide slots 314, funnel 304 and a first hub assembly 326. First hub assembly 326 may include or otherwise be connected to a first electric motor 316 as well as a first rotor 324 whereby first electric motor 316 and first rotor 324 are a part of airflow system 120 in communication with and responding to signals from control system 105.

First hub assembly 326 may have a ring-shaped body that has with one or more prongs 327 extending outward whereby each prong 327 may be independently received into the one or more guide slots 314 allowing the first hub assembly 326 to be in a slidable engagement with tubular shaped housing 302 near outlet end 310. In this embodiment there are three prongs 327 and three guide slots 314. However this is for illustrative purposes only and there may be any number of prongs 327 and guide slots 314. Once attached assembly first hub assembly 326 may locked to tubular shaped housing 302 such that first hub assembly 326 may not rotate and only be removed when air purification assembly 100 is disassembled. First electric motor 316 may have two power connection points 320 and 322 that each independently go from the first electric motor 316 up one of prongs 327 of first hub assembly 326 and into the one or more guide slots 314. First electric motor 316 may be a 2000 CFM 54-watt electric motor, but in further embodiments, any suitable electric motor may be used.

Figure 6:
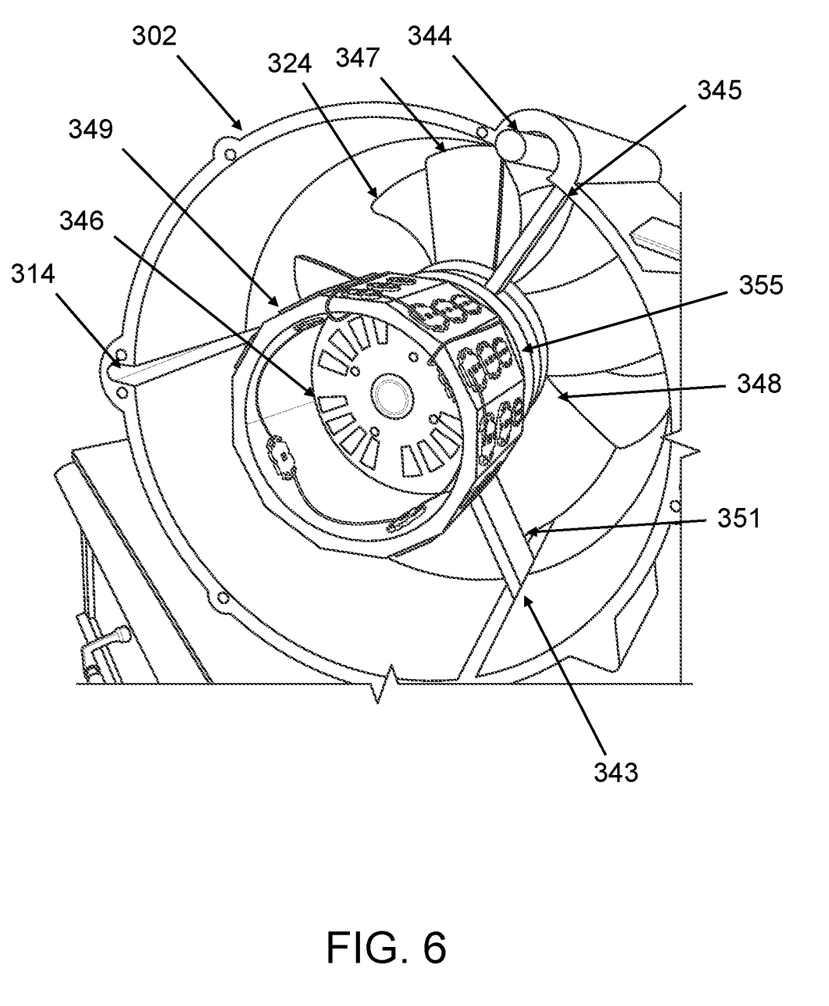
FIG. 6 shows a rear view of the air purification assembly displaying the second hub assembly.
Figure 8:
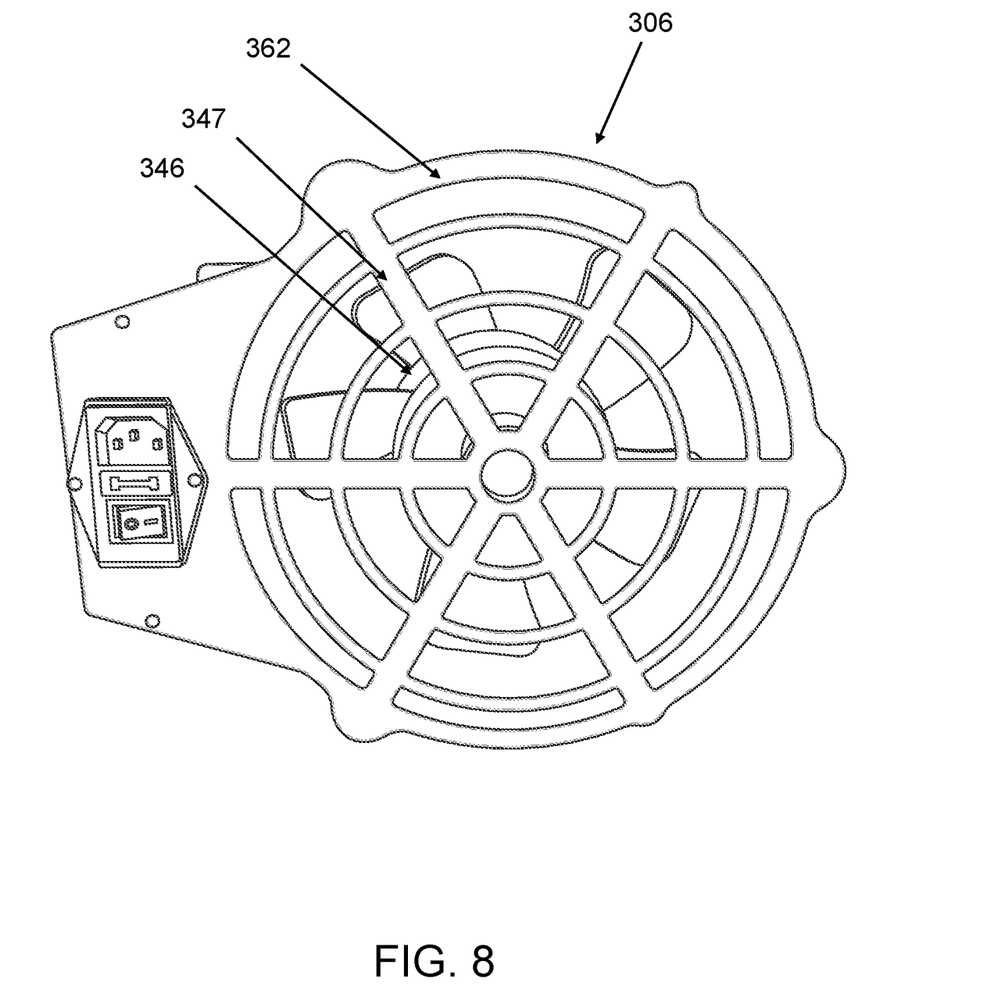
FIG. 8 shows an illustration of the end cap of the air purification assembly.

In a similar manner, as illustrated in FIG. 6, second hub assembly 348 may include or otherwise be connected to second electric motor 346 and second rotor 347 whereby second electric motor 346 and second rotor 347 are a part of airflow system 120 which is in communication with and responds to signals from control system 105. Second hub assembly 348 may have a ring-shaped body that has with one or more prongs 351 extending outward whereby each prong 351 may be independently received into the one or more guide slots 314 allowing the second hub assembly 348 to be in a slidable engagement with tubular shaped housing 302. Once attached assembly second hub assembly 348 may locked to tubular shaped housing 302 such that second assembly 348 may not rotate and only be removed when air purification assembly 100 is disassembled. Guide slots 314 may have one or more gaps, protrusions, recesses, or indents whereby the gaps may be positioned between second hub assembly 348 and end cap 362 to secure second hub assembly 348 in place and prevent it from sliding along guide slots 314. End cap 362 is further illustrated in FIG. 8

Second electric motor 348 may have two power connection points 343 and 345 that each independently go from the second electric motor 346 up one of prongs 351 of second hub assembly 3348 and into the one or more guide slots 314. Second electric motor 346 may be a 2000 CFM 54-watt electric motor, but in further embodiments, any suitable electric motor may be used.

One or more conductive spacers such as conductive spacers 344 may be placed independently into the one or more guide slots 314. These conductive spacers 344 serve the dual purpose of keeping separated, and in place, first hub assembly 326 and second hub assembly 348, as well as allows the transfer of power between first electric motor 316 and second electric motor 346.

As discussed with power system 130 in some embodiments second electric motor 346 may be powered by a wired connection, such as plugged into an electrical outlet, or powered by battery. In some embodiments, the battery may be stored inside the air purification assembly's 100 top mount 319. After second electric motor 346 is powered, power may travel from second electric motor 346 to power connection point 343, through a conductive spacer 344 positioned inside one of guide slots 314 to power point 322, powering first electric motor 316, then leaving from first electric motor 316 to power connection point 320, traveling to a second conductive spacer 344 located in another guide slot 314 to power connection point 345 to complete the electric circuit.

First electric motor 316 may be connected to first rotor 324. First rotor 324 may be an outlet rotor that blows the pressurized air between second rotor 347 and first rotor 324 out of tubular shaped housing 302. In one non-limiting embodiment, first rotor 324 may have five blades angled at a 29-degree angle rotating counterclockwise. In other non-limiting embodiments, first rotor 324 may have any number of blades, be rotated clockwise or have blades angled at different degrees.

Second electric motor 346 may be connected to second rotor 347. Second rotor 347 may be located at the inlet end of the air purification assembly 100, and sucks in the air through the end cap. In one non-limiting embodiment, the second rotor 347 may have five blades angled at a 45-degree angle rotating counterclockwise. In other non-limiting embodiments, second rotor 347 may have any number of blades, rotate clockwise or have different angle blades.

First rotor 324 and the second rotor 347 may both rotate in the same direction, but their blade angles are opposed to each other in opposite directions. After the air is sucked into tubular shaped body 302 by second rotor 347, the air is pressurized between the first rotor 324 and second rotor 347, and first rotor 324 blows the pressurized air out of air purification assembly 100 at a high intensity and volume.

Ring-shaped assembly 349 may be configured to attach around the outer circumference of second electric motor 346. Ring-shaped assembly 349 may be made out of an aluminum alloy pipe having a 4" diameter, 2½" length and 0.38" thickness with one or more UV-C LEDs 355 positioned on the outer surface of ring shaped assembly 349. The aluminum alloy pipe acts as a base to mount UV-C LEDs 355 on while dispersing the heat UV-C LEDs 355 generate. In other non-limiting embodiments ring-shaped assembly may be any size or made out of any material.

Ring-shaped assembly 349 sleeves onto the outside of second motor 346 of air purification assembly 100, allowing air to pass around and through the ring-shaped assembly 349, keeping UVC LEDs 355 at ambient room temp (typically 68-72 degrees Fahrenheit). In this embodiment, this ensures proper operation of UVC LEDs 355 due to the nature of it being inefficient in heat dissipation for large amounts of UVC power. When mounted on the ring-shaped assembly 349, UVC LEDs 355 may be positioned 2" from interior surface of tubular shaped body 302. UVC LEDs 355 emit light between 265-275 nm (mutates the DNA of microorganisms). These UVC LEDs 355 are maximally effective at a 2" range. UVC LEDs 355 have a tendency to overheat and become less efficient. The air purification assembly 100 keeps them at room temperature and functioning at peak capacity.

UV-C LEDs 355 may communicate via control system 105 with a microprocessor or driver via a bus. Bus may communicate with microprocessor which controls UV-C LEDs 355 to turn off or on in specific increments of time so UV-C LEDs may last longer than if they were to run continuously. Microprocessor may also adjust output for maximum UV-C LEDs 355 power and maximum efficiency. Power is brought to ring-shaped assembly 349 from Driver in parallel and low voltage via copper inlays in second hub assembly 348 of the air purification assembly 100. The Positive (+) and Negative (−) leads from the microprocessor are connected to bus which is embedded in second hub assembly 348. UV-C LEDs 355 may be powered in series off of bus and may be in pre-arranged even numbered sets (2, 4, 6, etc.) for exact power to each individual UV-C LED 355. In some non-limiting embodiments UV-C LEDs 355 are 0.013-0.1 mW UVC spectrum (265-275 nm) LEDs, programmable driver 0-54V 0-1100 mW, and bus may be built into second hub assembly 348.

Figure 7:
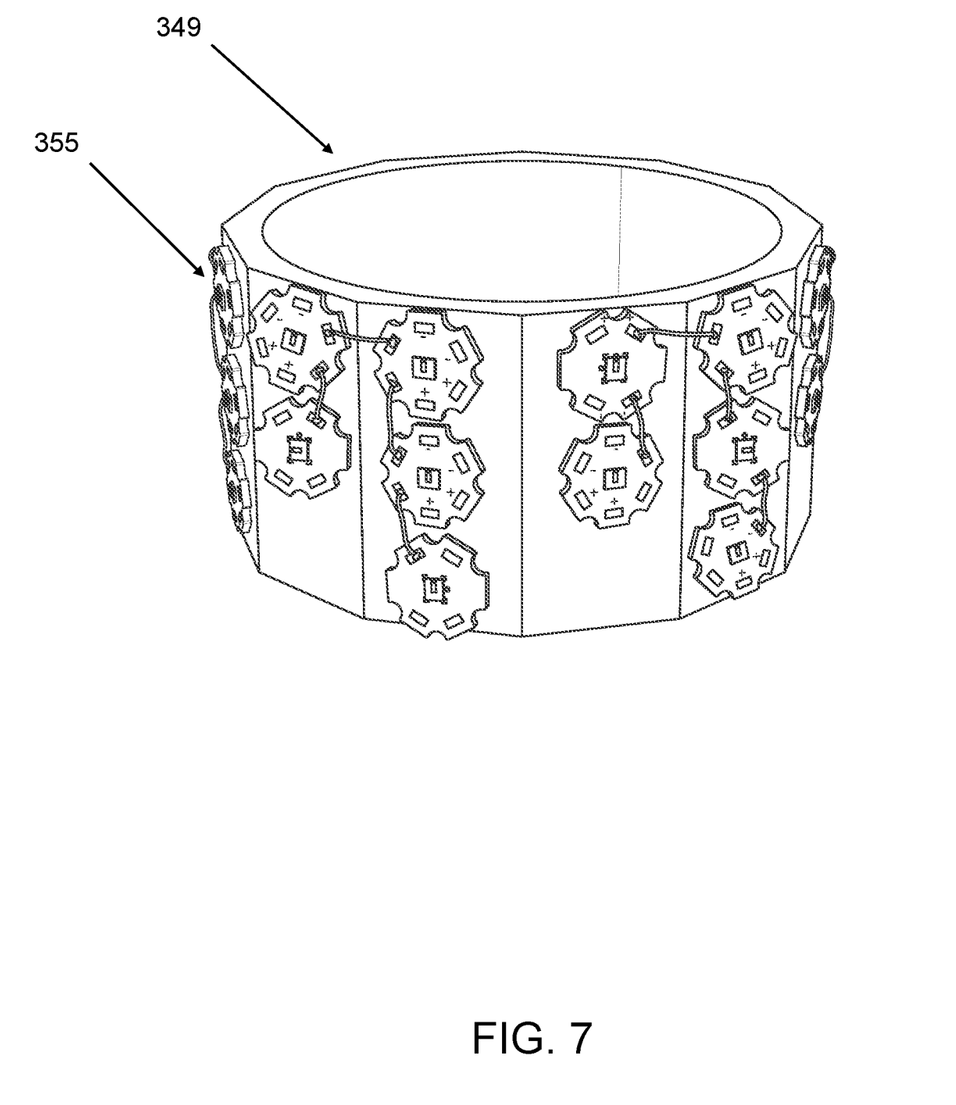
FIG. 7 shows an embodiment of the ring shaped assembly.

In a further non-limiting embodiment, ring-shaped assembly 349 may be a 4″ round aluminum allow pipe with ⅜″ thickness as illustrated in FIG. 7. In this embodiment the outside of the pipe is machined to 12, 1′×2½′ flat space running the length of the pipe. Each flat space may hold three StarPad heat sinks that are approximately the size of a nickel (~25/32″). Each StarPad may hold a 60 mm PCB board and an individual UVC LED 355. There may be four more flat spaces with similar configurations mounted on the inside of the 4″ aluminum allow pipe. The inside of air purification assembly 100 in immediate vicinity of ring-shaped assembly 349 may be covered in aluminum tape to reflect the UVC LED's 355 light back towards the center of air purification assembly 100.

Air purification assembly 100 may have one or more sensors as a part of sensor system 110 which may include a plurality of detectors mounted or otherwise connected to air purification assembly 100 in communication with control system 105. Sensor system 110 may have one or more temperature sensors for sensing temperature within or around air purification assembly 100 and providing a temperature signal, one or more humidity sensors for sensing relative humidity within or around air purification assembly 100 and providing a humidity signal, or other type of sensors and transducers may be employed. Sensors may be arranged in any number of configurations and arrangements.

Sensor system 110 may have a temperature sensor in any suitable position with respect to air purification assembly 100 in order to measure, either directly or indirectly, a temperature associated with or in the general proximity (including inside and outside) of air purification assembly 100 in any suitable manner. For example, the temperature sensor can include one or more (or any suitable combination) of the following components or devices: a resistive element, a strain gauge, a temperature probe, a thermistor, a resistance temperature detector (RTD), a thermocouple, a thermometer (liquid-in-glass, filled-system, bimetallic, infrared, spot radiation), a semiconductor, an optical pyrometer (radiation thermometer), a fiber optic device, a phase change device, a thermowell, or a thermal imager.

Control system 105 may measure the temperature and the microprocessors then compare the received input value from sensor system 110 using a comparison function and evaluate the input data against a setting or expectation of a certain reference value stored within the memory of control system 105. Control system 105 analyzes received input value from sensor system 110 using a comparison function and evaluate the input data to determine when air purification assembly 100 should turn off. Control system 105 may be in communication with a thermal protection device whereby the device may trip and shut down the electrical flow to first and second motor. This will allow first and second motor to cool down or advert avert a complete failure of air flow assembly 100.

Figure 9:
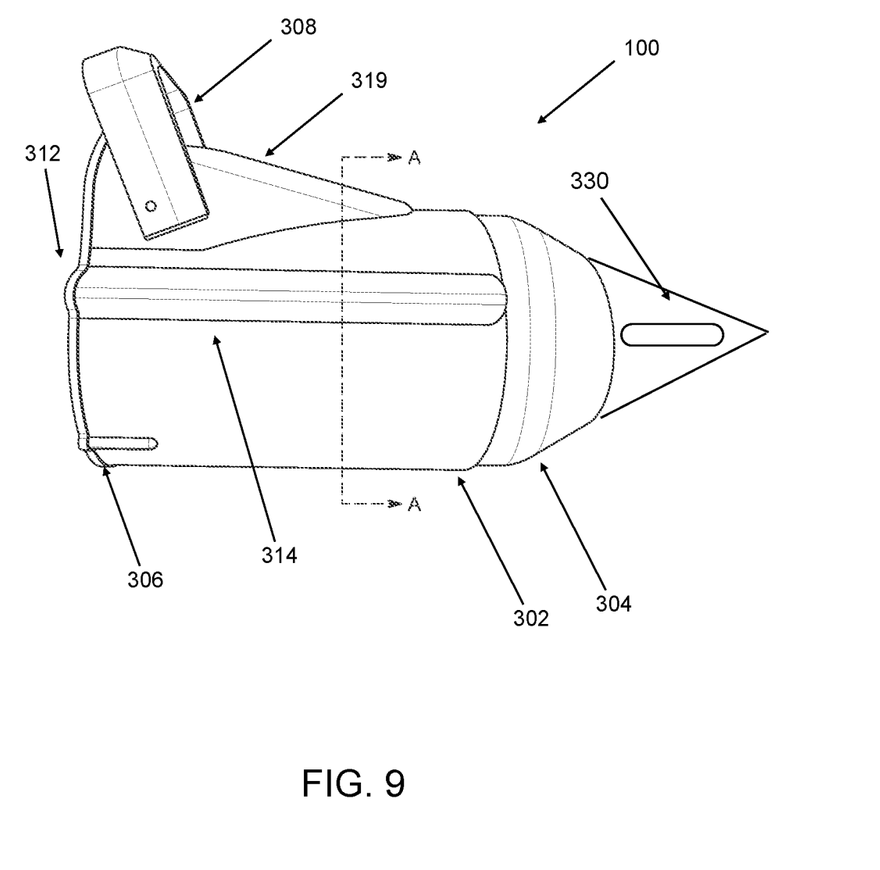
FIG. 9 shows an illustration of an embodiment of air purification assembly including a cone cap.

In an additional embodiment of air purification assembly 100 first rotor 324 may be mounted, on the opposite side of first hub assembly 326 closer towards the center of air purification assembly 100. A cone cap 330 may be mounted onto first electric motor 316. Cone cap 330 may face towards the outlet end of the air blower assembly whereby cone cap may provide further pressuring of the air, after it is blown by first rotor 324, by compressing the air between the cone cap and funnel 304 as it is blown out the outlet end of the air blower assembly 100. Cone cap 330 may have one or more apertures 331. Cone cap 330, in one embodiment, as illustrated in FIG. 9, may also be included on the FIG. 4 first hub assembly.

Advantageously, the present description provides one or more embodiments of various types of air purification assemblies. Each air purification assembly depicted herein provides advantages that overcome shortcomings of other types of air blowers and air purifying devices that are used conventionally. Further, the various embodiments shown in the Figures and described herein accommodate different sized air blowers (including single or multi-bladed rotor assemblies) and may be used in various applications, including, but not limited to, purification of air and increased air blower volume. It is noted that the various embodiments of air purification assemblies presented herein may be used in many other ways other than to provide large voluminous movement of air. For example, the various air purification assemblies can be used to provide air purification. Thus, the various embodiments described in the present description include a number of novel and helpful components that provide enhanced air movement apparatuses to benefit a user.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. An air purification assembly comprising:
   an inlet and an outlet;
   a housing component having a first end and a second end;
   a funnel having a first end and second end, the outlet at the first end of the funnel, the second end of the funnel connected to the second end of the housing component;
   a first hub assembly having a first motor and a first rotor, the first rotor having one or more blades;

a second hub assembly having a second motor and a second rotor, the second rotor having one or more blades; and a ring-shaped assembly configured to attach around an outer circumference of said second motor, wherein the ring-shaped assembly has one or more UV-C LED.

2. The air purification assembly from claim 1 further comprising: one or more guide slots positioned along an inner circumference of the housing component wherein the first hub assembly and the second hub assembly are slidably engaged with the one or more guide slots.

3. The air purification assembly from claim 2 further comprising: one or more conductive spacers positioned in the one or more guide slots, wherein the one or more conductive spacers are configured to transfer electricity between the first motor and the second motor.

4. The air purification assembly from claim 1 further comprising: an end cap, the end cap connected to the housing component at the first end, the end cap having one or more grooves configured to allow air to be sucked into the air purification assembly by the second motor.

5. The air purification assembly from claim 1, wherein the one or more blades of the second rotor are orientated at a greater angle than the one or more blades of the first rotor.

6. The air purification assembly from claim 5, wherein the one or more blades of the second rotor are at a 45-degree angle and the one or more blades of the first rotor are at a 29-degree angle.

7. The air purification assembly from claim 6, wherein the one or more blades of the first rotor and second rotor are configured to rotate counterclockwise.

8. The air purification assembly from claim 1, wherein the first motor and the second motor are electric motors.

9. An air purification assembly comprising:
a ring-shaped assembly, wherein the ring-shaped assembly has one or more UV-C LED, wherein one or more flat spaces running a length of the ring-shaped assembly, the one or more flat spaces holding one or more heat sinks having a PCB board and an individual UV-C LED.

10. The air purification assembly from claim 9 further comprising: a driver wherein the UV-C LED communicates with the driver via a bus.

11. The air purification assembly from claim 10, the driver further configured to adjust an output of the UV-C LED.

12. The air purification assembly from claim 9 further comprising:
an inlet and an outlet;
a housing component having a first end and a second end;
a funnel having a first and second end, the outlet at the first end of the funnel, the second end of the funnel connected to the second end of the housing component;
a first hub assembly having a first motor and a first rotor, the first rotor having one or more blades;
a second hub assembly having a second motor and a second rotor, the second rotor having one or more blades; and
one or more guide slots positioned along an inner circumference of the housing component wherein the first hub assembly and the second hub assembly are slidably engaged with the one or more guide slots.

13. The air purification assembly from claim 12, further comprising: one or more conductive spacers positioned in the one or more guide slots, wherein the one or more conductive spacers are configured to transfer electricity between the first motor and the second motor.

14. The air purification assembly from claim 12 further comprising: an end cap, the end cap connecting to the housing component at the first end, the end cap having one or more grooved configured to allow air to be sucked in by the second motor.

15. The air purification assembly from claim 14, wherein the one or more blades of the second rotor are at a 45-degree angle and the one or more blades of the first rotor are at a 29-degree angle, the one or more blades of the first rotor and second rotor rotating counterclockwise, and the one or more blades of the first rotor and second rotor facing opposite of each other.

16. An air purification assembly comprising:
an inlet and an outlet;
a housing component having a first end and a second end;
a funnel having a first end and second end, the outlet at the first end of the funnel, the second end of the funnel connected to the second end of the housing component;
a first hub assembly having a first motor and a first rotor, the first rotor having one or more blades;
a second hub assembly having a second motor and a second rotor, the second rotor having one or more blades; and
an end cone cap, the end cone cap connected to the first motor, the end cone cap facing towards the outlet wherein the end cone cap is configured to provide further pressuring of air after it is blown by the first rotor by compressing the air between the end cone cap and the funnel as it is blown out the outlet.

* * * * *